(12) United States Patent
Vernier et al.

(10) Patent No.: US 7,786,146 B2
(45) Date of Patent: Aug. 31, 2010

(54) DERIVATIVES OF 5-AMINO-4,6-DISUBSTITUTED INDOLE AND 5-AMINO-4,6-DISUBSTITUTED INDOLINE AS POTASSIUM CHANNEL MODULATORS

(75) Inventors: Jean-Michel Vernier, Laguna Niguel, CA (US); Huanming Chen, Irvine, CA (US); Jianlan Song, Cerritos, CA (US)

(73) Assignee: Valeant Pharmaceuticals International, Aliso Viejo, CA (US)

( * ) Notice: Subject to any disclaimer, the term of this patent is extended or adjusted under 35 U.S.C. 154(b) by 0 days.

(21) Appl. No.: 12/189,709

(22) Filed: Aug. 11, 2008

(65) Prior Publication Data

US 2009/0137635 A1    May 28, 2009

Related U.S. Application Data

(60) Provisional application No. 60/964,526, filed on Aug. 13, 2007.

(51) Int. Cl.
| A61K 31/4439 | (2006.01) |
| A61K 31/404 | (2006.01) |
| C07D 401/06 | (2006.01) |
| C07D 209/08 | (2006.01) |

(52) U.S. Cl. .................. 514/339; 514/415; 546/277.4; 548/510

(58) Field of Classification Search ............. 514/339, 514/419; 548/495; 546/277.4
See application file for complete search history.

(56) References Cited

U.S. PATENT DOCUMENTS

| 4,554,281 A | 11/1985 | vonBebenburg et al. |
| 4,923,858 A | 5/1990 | Engel et al. |
| 5,032,591 A | 7/1991 | Evans et al. |
| 5,234,947 A | 8/1993 | Cherksey |
| 5,262,419 A | 11/1993 | Aberg et al. |
| 5,384,330 A | 1/1995 | Dieter et al. |
| 5,428,039 A | 6/1995 | Cohen |
| 5,643,921 A | 7/1997 | Grover |
| 5,679,706 A | 10/1997 | D'Alonzo et al. |
| 5,800,385 A | 9/1998 | Demopulos et al. |
| 5,849,789 A | 12/1998 | Rostock et al. |
| 5,852,053 A | 12/1998 | Rostock et al. |
| 5,858,017 A | 1/1999 | Demopulos et al. |
| 5,860,950 A | 1/1999 | Demopulos et al. |
| 5,914,425 A | 6/1999 | Meisel et al. |
| 6,117,900 A | 9/2000 | Rundfeldt et al. |
| 6,218,411 B1 | 4/2001 | Koga |
| 6,265,417 B1 | 7/2001 | Carroll |
| 6,326,385 B1 | 12/2001 | Wickenden et al. |
| 6,348,486 B1 | 2/2002 | Argentieri et al. |
| 6,395,736 B1 | 5/2002 | Parks et al. |
| 6,469,042 B1 | 10/2002 | Hewawasam et al. |
| 6,472,165 B1 | 10/2002 | Rundfeldt et al. |
| 6,495,550 B2 | 12/2002 | McNaughton-Smith et al. |
| 6,538,004 B2 | 3/2003 | Drizin |
| 6,538,151 B1 | 3/2003 | Meisel et al. |
| 6,589,986 B2 | 7/2003 | Bowlby et al. |
| 6,593,335 B1 | 7/2003 | Carroll |
| 6,737,422 B2 | 5/2004 | McNaughton-Smith et al. |
| 7,045,551 B2 | 5/2006 | Wu et al. |
| 7,160,684 B2 | 1/2007 | Argentieri et al. |
| 7,309,713 B2 | 12/2007 | Rundfeldt et al. |
| 2002/0013349 A1 | 1/2002 | Wickenden et al. |
| 2002/0015730 A1 | 2/2002 | Hoffmann et al. |
| 2002/0183395 A1 | 12/2002 | Argentieri |
| 2004/0198724 A1 | 10/2004 | McNaughton-Smith et al. |
| 2005/0089473 A1 | 4/2005 | Black et al. |
| 2005/0089559 A1 | 4/2005 | Szelenyi et al. |
| 2005/0090547 A1 | 4/2005 | Szelenyi et al. |
| 2005/0202394 A1 | 9/2005 | Dobson |
| 2005/0277579 A1 | 12/2005 | Krishnan et al. |
| 2007/0066612 A1 | 3/2007 | Khanzhin et al. |

FOREIGN PATENT DOCUMENTS

| DE | 3337593 | 10/1983 |
| EP | 0 343 429 | 5/1989 |
| EP | 1 334 972 | 8/2003 |
| WO | WO 00/55137 | 9/2000 |
| WO | WO 01/01970 | 1/2001 |
| WO | WO 01/09612 | 2/2001 |
| WO | WO 02/080898 | 10/2002 |
| WO | WO 03/020706 | 3/2003 |

(Continued)

OTHER PUBLICATIONS

Patani et al., Bioisosterism: A Rational Approach in Drug Design, 1996, Chem. Rev., 96, 3147-3176.*

(Continued)

Primary Examiner—Kamal A Saeed
Assistant Examiner—Kristin Bianchi
(74) Attorney, Agent, or Firm—McDermott Will & Emery LLP

(57) ABSTRACT

This invention provides compounds of formula I

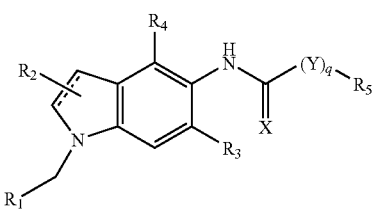

where the dashed line represents an optional double bond; where $R_1$ is phenyl, naphthyl, pyridyl, pyrimidyl, pyrrolyl, imidazolyl, pyrazyl, furyl, thienyl, oxazolyl, isoxazolyl, thiazolyl, or isothiazolyl, optionally substituted, and other substituents are defined herein. Such compounds are potassium channel modulators.

15 Claims, No Drawings

FOREIGN PATENT DOCUMENTS

| | | |
|---|---|---|
| WO | WO 03/097586 | 11/2003 |
| WO | WO 2004/058739 | 7/2004 |
| WO | WO 2004/080950 | 9/2004 |
| WO | WO 2004/082677 | 9/2004 |
| WO | WO 2004/096767 | 11/2004 |
| WO | WO 2004/105795 | 12/2004 |
| WO | WO 2005/048975 | 6/2005 |
| WO | WO 2005/087754 | 9/2005 |
| WO | WO 2005/100349 | 10/2005 |
| WO | WO 2006/029623 | 3/2006 |
| WO | WO 2006/092143 | 9/2006 |
| WO | WO 2008/024398 | 2/2008 |
| WO | WO 2008/066900 | 6/2008 |

OTHER PUBLICATIONS

Vippagunta et al., Crystalline solids, 2001, Advanced Drug Delivery Reviews, 48, 3-26.*

Armand et al., "Effects of retigabine (D-23129) on different patterns of epileptiform activity induced by 4-aminopyridine in rat entorhinal cortex hippocampal slices," *Naunyn-Schmiedeberg's Arch Pharmacol* 359:33-39 (1999).

Armijo et al., "Ion channels and epilepsy," *Curr Pharm Des.* 11:1975-2003 (2005).

Barhanin, M:, et al., "K,LQT1 and ISK (minK) proteins associate to form the $I_{Ks}$ cardiac potassium current," *Nature* 384(6604):78-80 (1996).

Beeby et al. "The synthesis and properties of 2:7-Disubstituted 1:2:3:4-tetrahydroisoquinolines," *J. Chem. Soc.* ¶ 385, 1799-1803 (1949).

Bialer et al., "Progress report on new antiepileptic drugs: a summary of the fourth Eilat conference (Eilat IV)," *Epilepsy Res.* 34:1-41 (1999).

Bialer, "Progress report on new antiepileptic drugs: a summary of the Sixth Eilat Conference (Eilat VI)," *Epilepsy Res.* 51:31-71 (2002).

Bialer, "Progress report on new antiepileptic drugs: a summary of the Seventh Eilat Conference (Eilat VII)," *Epilepsy Res.* 61:1-48 (2004).

Biervert et al., "A potassium channel mutation in neonatal human epilepsy," *Science* 279:403-406 (1998).

Blackburn-Munro and Jensen, "The anticonvulsant retigabine attenuates nociceptive behaviours in rat models of persistent and neuropathic pain," *Eur J Pharmacol.* 460: 109-116 (2003).

Brown and Adams, "Muscarinic suppression of a novel voltage-sensitive K+ current in a vertebrate neurone," *Nature* 283:673-676 (1980).

Brown, D.A., Ion Channels, T. Narahashi, Ed. (Plenum Press, New York) pp. 55-94 (1988).

Charlier et al., "A pore mutation in a novel KQT-like potassium channel gene in an idiopathic epilepsy family," *Nat Genet.* 18:53-55 (1998).

Cooper et al., "Colocalization and coassembly of two human brain M-type potassium channel subunits that are mutated in epilepsy." *Proc Natl Acad Sci USA* 97:4914-4919 (2000).

Delmas and Brown, "Pathways modulating neural KCNQ/M (Kv7) potassium channels," *Nat Rev Neurosci.* 6:850-862 (2005).

Dickenson al., "Neurobiology of neuropathic pain: mode of action of anticonvulsants," *Eur. J. Pain* 6:51-60 (2002).

Dost et al., "The anticonvulsant retigabine potently suppresses epileptiform discharges in the low Ca ++ and low Mg++ model in the hippocampal slice preparation," *Epilepsy Res.* 38:53-56 (2000).

Friedel and Fitton, "Flupirtine: a review of its analgesic properties, and therapeutic efficacy in pain states," *Drugs* 45:548-569 (1993).

Hiller et al., "Retigabine N-glucuronidation and its potential role in enterohepatic circulation," *Drug Metab Dispos.* 27(5):605-612 (1999).

Hunt and Mantyh, "The molecular dynamics of pain control," *Nat Rev Neurosci.* 2:83-91 (2001).

Jentsch, "Neuronal KCNQ potassium channels; physiology and role in disease," *Nat. Rev Neurosci.*, 1:21-30 (2000).

Jiang et al., "X-ray structure of a voltage-dependent K+ channel," *Nature* 423:33-41.

Kharkovets et al., "Mice with altered KCNQ4 K+ channels implicate sensory outer hair cells in human progressive deafness," *EMBO J* 25:642-652 (2006).

Kibbe *Handbook of Pharmaceutical Excipients* (Pharmaceutical Press, London) (2000).

Kubisch et al., "KCNQ4, a novel potassium channel expressed in sensory outer hair cells, is mutated in dominant deafness," *Cell* 96:437-446 (1999).

Lamas et al., "Effects of a cognition-enhancer, linopirdine (DuP 996), on M-type potassium currents ($I_{K(M)}$) and some other voltage- and ligand-gated membrane currents in rat sympathetic neurons," *Eur. J Neurosci.*, 9:605-616 (1997).

Lee et al., "Structure of the KvAP voltage-dependent K+ channel and its dependence on the lipid membrane," *Proc Natl Acad Sci USA* 102:15441-15446 (2005).

Long et al., "Crystal Structure of a Mammalian voltage-dependent Shaker family K+ channel," *Science* 309:897-903 (2005).

Main et al., "Modulation of KCNQ2/3 potassium channels by the novel anticonvulsant retigabine," *Mol. Pharmacol.* 58:253-262 (2000).

Marrion, "Control of M-currents," *Annu Rev Phvsiol.* 59:483-504 (1997).

Parcej and Eckhardt-Strelau, Structural characterization of neuronal voltage-sensitive K+ channels heterologously expressed in *Pichia pastoris, J Mol Biol* 333:103-116 (2003).

Passmore et al., "KCNQ/M currents in sensory neurons: significance for pain therapy," *J. Neurosci.* 23:7227-7236 (2003).

Porter et al., "Retigabine," *Neurotherapeutics* 4:149-154 (2007).

Reich et al., "Design and synthesis of novel 6,7-imidazotetrahydroquinoline inhibitors of thymidylate synthase using iterative protein crystal structure analysis," *J. Med. Chem.* 35:847-858 (1992).

Rogawski, MA, "KCNQ2/KCNQ3 K+ channels and the molecular pathogenesis of epilepsy: implications for therapy," *Trends Neurosci.* 23:393-398 (2000).

Rostock et al., "A new anticonvulsant with broad spectrum activity in animal models of epileptic seizures," *Epilepsy Res.*23:211-223 (1996).

Rundfeldt et al., "Multiple actions of the new anticonvulsant D-23129 on voltage-gated inward currents and GABA-induced currents in cultured neuronal cells (abstract)," *Naunyn-Schmiedeberq's Arch Pharmacol* 351 (Suppl):R160 (1995).

Rundfeldt, "Characterization of the K+ channel opening effect of the anti-convulsant retigabine in PC12 cells," *Epilepsy Res.*35:99-107 (1999).

Rundfeldt, "The new anticonvulsant retigabine (D23129) acts as an opener of K+ channels in neuronal cells," *Eur J Pharmacol.* 336:243-249 (1997).

Schroeder et al., "KCNQ5, a novel potassium channel broadly expressed in brain, mediates M-type currents," *J. Biol. Chem.* 275:24089-24095 (2000).

Schroeder, "Moderate loss of function of cyclic-Amp-modulated KNCQ2/KCNQ3 K+ channels causes epilepsy," *Nature* 396:687-690 (1998).

Singh et al., "A novel potassium channel gene, KCNQ2, is mutated in an inherited epilepsy of newborns," *Nat Genet.* 18:25-29 (1998).

Suzuki and Dickenson, "Neuropathic pain: nerves bursting with excitement," *NeuroReport* 11:R17-R21 (2000).

Tatulian and Brown, "Effect of the KCNQ potassium channel opener retigabine on single KCNQ2/3 channels express in CHO cells," *J Physiol.* 549:57-63 (2003).

Tatulian et al., "Activation of expressed KCNQ potassium currents and native neuronal M-type potassium currents by the anti-convulsant drug retigabine," *J. Neurosci.* 21:5535-5545 (2001).

Tober et al., "D-23129: a potent anticonvulsant in the amygdala kindling model of complex partial seizures," *Eur J Pharmacol*, 303:163-169 (1996).

Von Bebenburg et al., "Substituierte Polyaminopyridine" *Chemiker-Zeitunq* 103:387-399 (1979). (German language article attached.).

Wang et al., KCNQ2 and KCNQ3 potassium channel subunits: molecular correlates of the M-channel, *Science* 282:1890-1893 (1998).

Wang et al., "Positional cloning of a novel potassium channel gene: KVLQT1 mutations cause cardiac arrhythmias," *Nat Genet* 12:17-23 (1996).

Watanbe et al., "Disruption of the epilepsy KCNQ2 gene results in neural hyperexcitability," *J. Neurochem* 75:28-33 (2000).

Wickenden et al., "KCNQ potassium channels: drug targets for the treatment of epilepsy and pain," *Exp. Opin Thera Patents* 14(4): 457-469 (2004).

Wickenden et al., "Retigabine, a novel anti-convulsant, enhances activation of KCNQ2/Q3 potassium channels," *Mol. Pharmacol.* 58:591-600 (2000).

Wuttke, "The new anticonvulsant retigabine favors voltage-dependent opening of the Kv7.2 (KCNQ2) channel by binding to its activation gate," *Mol. Pharmacol.* 67:1009-1017 (2005).

\* cited by examiner

DERIVATIVES OF 5-AMINO-4,6-DISUBSTITUTED INDOLE AND 5-AMINO-4,6-DISUBSTITUTED INDOLINE AS POTASSIUM CHANNEL MODULATORS

CROSS-REFERENCE TO RELATED APPLICATION

This application claims priority under 35 U.S.C. §119(e) to U.S. Provisional Application No. 60/964,526, filed Aug. 13, 2007, which is incorporated by reference herein in its entirety.

FIELD OF THE INVENTION

This invention concerns novel compounds that modulate potassium channels. The compounds are useful for the treatment and prevention of diseases and disorders which are affected by activities of potassium ion channels. One such condition is seizure disorders.

BACKGROUND OF THE INVENTION

Epilepsy is a well-known neurological disease, found in about 3% of the population. Approximately 30% of patients with epilepsy do not respond to currently available therapies. Retigabine (N-[2-amino-4-(4-fluorobenzylamino) phenyl] carbamic acid, ethyl ester] (U.S. Pat. No. 5,384,330) has been found to be an effective treatment of a broad range of models of seizure disorders, and it appears to have an unusual mechanism of action. Bialer, M. et al., *Epilepsy Research* 1999, 34, 1-41; Wuttke, T. V., et al., *Mol. Pharmacol.* 2005, 67, 1009-1017. Retigabine has also been found to be useful in treating pain, including neuropathic pain. Blackburn-Munro and Jensen, *Eur. J. Pharmacol.* 2003, 460, 109-116; Wickenden, A. D. et al., *Expert Opin. Ther. Patents*, 2004, 14(4).

"Benign familial neonatal convulsions," an inherited form of epilepsy, has been associated with mutations in the KCNQ2/3 channels. Biervert, C. et al., *Science* 1998, 27, 403-06; Singh, N. A., et al., *Nat. Genet.* 1998, 18, 25-29; Charlier, C. et al., *Nat. Genet.* 1998, 18, 53-55; Rogawski, *Trends in Neurosciences* 2000, 23, 393-398. Subsequent investigations have established that one important site of action of retigabine is the KCNQ2/3 channel. Wickenden, A. D. et al., *Mol. Pharmacol.* 2000, 58, 591-600; Main, M. J. et al., *Mol. Pharmacol.* 2000, 58, 253-62. Retigabine has been shown to increase the conductance of the channels at the resting membrane potential, with a possible mechanism involving binding of the activation gate of the KCNQ 2/3 channel. Wuttke, T. V., et al., *Mol. Pharmacol.* 2005, op. cit. With increased sophistication of research in this area, retigabine has also been shown to increase neuronal M currents and to increase the channel open probability of KCNQ 2/3 channels. Delmas, P. and Brown, D. A. *Nat. Revs Neurosci.*, vol. 6, 2005, 850-62; Tatulian, L. and Brown, D. A., J. Physiol., (2003) 549, 57-63.

The most therapy-resistant type of seizure is the so-called "complex partial seizure." Retigabine has been found to be particularly potent in models for drug-refractory epilepsy. Retigabine is also active in several other seizure models. Because of retigabine's broad spectrum of activity and unusual molecular mechanism, there is hope that retigabine will be effective in management of several seizure types, including the complex partial seizure, and in treatment of hitherto untreatable forms of epilepsy. Porter, Roger J., Nohria, Virinder, and Rundfeldt, Chris, *Neurotherapeutics*, 2007, vol. 4, 149-154.

The recognition of retigabine as a potassium channel modulator has inspired a search for other—and, hopefully, better—potassium channel modulators among compounds with structural features similar to those of retigabine.

BRIEF DESCRIPTION OF THE INVENTION

In one embodiment, this invention provides a compound of formula I

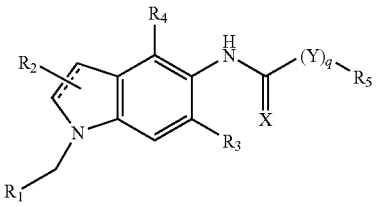

where the dashed line represents an optional double bond; where $R_1$ is phenyl, naphthyl, pyridyl, pyrimidyl, pyrrolyl, imidazolyl, pyrazyl, furyl, thienyl, oxazolyl, isoxazolyl, thiazolyl, or isothiazolyl, optionally substituted with one or two substituents selected independently from halogen, $C_1$-$C_6$ alkyl, mono-halo $C_1$-$C_6$ alkyl, di-halo $C_1$-$C_6$ alkyl, $CF_3$, CN, S—$C_1$-$C_6$ alkyl, or O—$C_1$-$C_6$ alkyl; $R_2$ is H, methyl, or halogen; $R_3$ and $R_4$ are, independently, $CF_3$, $OCF_3$, $OC_1$-$C_3$ alkyl, halo or $C_1$-$C_3$ alkyl, where the $C_1$-$C_3$ alkyl groups are optionally substituted with one or more halogen atoms; X=O or S; Y is O or S; q=1 or 0; $R_5$ is $C_1$-$C_6$ alkyl where the $C_1$-$C_6$ alkyl alkyl group is optionally substituted with one or two groups selected, independently, from OH, OMe, OEt, F, $CF_3$, Cl, or CN; $(CHR_6)_w C_3$-$C_6$ cycloalkyl, $(CHR_6)_w CH_2 C_3$-$C_6$ cycloalkyl, $CH_2(CHR_6)_w C_3$-$C_6$ cycloalkyl, $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, $C_2$-$C_6$ alkynyl, $Ar_1$, $(CHR_6)_w Ar_1$, $CH_2(CHR_6)_w Ar_1$, or $(CHR_6)_w CH_2 Ar_1$, where w=0-3, $Ar_1$ is phenyl, pyridyl, pyrrolyl, thienyl, or furyl, and $R_6$ is hydrogen, methyl, halogen, or methoxy; where all cyclic groups are optionally substituted with one or two substituents selected independently from $C_1$-$C_3$ alkyl, halogen, OH, OMe, SMe, CN, $CH_2F$, and trifluoromethyl; or a pharmaceutically acceptable salt thereof. Such compounds are potassium channel modulators.

In another embodiment, this invention provides a composition comprising a pharmaceutically acceptable carrier and one or more of the following: a pharmaceutically effective amount of a compound of formula I; a pharmaceutically effective amount of a pharmaceutically acceptable salt thereof; a pharmaceutically effective amount of a pharmaceutically acceptable ester thereof.

In yet another embodiment, this invention provides a method of preventing or treating a disease or disorder which is affected by modulation of voltage-gated potassium channels, comprising administering to a patient in need thereof a therapeutically effective amount of a compound of formula I or a salt or ester thereof.

In another embodiment, this invention provides or contemplates a composition comprising a pharmaceutically acceptable carrier and at least one of the following: i) a pharmaceutically effective amount of a compound of formula I; ii) a pharmaceutically acceptable salt thereof; iii) a pharmaceutically acceptable ester thereof; iv) a pharmaceutically acceptable solvate thereof.

In another embodiment, this invention provides or contemplates a method of treating or preventing a disease or disorder which is affected by enhancement of neural M currents comprising administering to a patient in need thereof one or more of the following: i) a pharmaceutically effective amount of a compound of formula I; ii) a pharmaceutically acceptable salt thereof; iii) a pharmaceutically acceptable ester thereof; iv) and a pharmaceutically acceptable solvate thereof.

In yet another embodiment, this invention provides a method of preventing or treating a disease or disorder which is affected by activation of voltage-gated potassium channels, comprising administering to a patient in need thereof one or more of the following: a pharmaceutically effective amount of a compound of formula I; ii) a pharmaceutically acceptable salt thereof; iii) a pharmaceutically acceptable ester thereof; and iv) a pharmaceutically acceptable solvate thereof.

In yet another embodiment, this invention provides or contemplates a method of treating or preventing a seizure disorder in a human comprising administering to a patient afflicted or potentially afflicted with such disorder one or more of the following: a pharmaceutically effective amount of a compound of formula I; ii) a pharmaceutically acceptable salt thereof; iii) a pharmaceutically acceptable ester thereof; iv) and a pharmaceutically acceptable solvate thereof.

In another embodiment, this invention provides or contemplates a pharmaceutical formulation for oral administration comprising a therapeutically effective amount of a compound of formula I and either an appropriate tabletting agent or an appropriate syrup for pediatric use.

In another embodiment, this invention provides or contemplates a tablet for oral administration comprising a therapeutically effective amount of a compound of formula I and an appropriate tabletting agent.

In another appropriate embodiment, this invention provides or contemplates a syrup for pediatric use comprising a solution or dispersion or suspension of a compound of formula I and an appropriate syrup.

In another embodiment, this invention contemplates a pharmaceutical formulation for administration to animals, including companion animals (dogs and cats), and livestock comprising a therapeutically effective amount of a compound of formula I and a veterinary acceptable carrier.

In another embodiment, this invention contemplates a method of preventing or treating a disease or disorder which is affected by activation of voltage-gated potassium channels comprising administering to an animal in need thereof one or more of the following: i) a pharmaceutically effective amount of a compound of formula I; ii) a pharmaceutically acceptable salt thereof; iii) a pharmaceutically acceptable ester thereof; iv) and a pharmaceutically acceptable solvate thereof.

In another embodiment, this invention contemplates a method of treating a seizure disorder in an animal comprising administering to an animal afflicted or potentially afflicted with such a disorder one or more of the following: i) a pharmaceutically effective amount of a compound of formula I; ii) a pharmaceutically acceptable salt thereof; iii) a pharmaceutically acceptable ester thereof; iv) and a pharmaceutically acceptable solvate thereof.

This invention includes all tautomers, salts, and stereoisomeric forms of compounds of formula I. This invention also includes all compounds of this invention where one or more atoms are replaced by a radioactive isotope thereof.

This invention provides or contemplates compounds of formula I above where NH—C(=X)—(Y)$_q$—R$_5$ is each of the following: NHC(=O)R$_5$, NHC(=O)OR$_5$, NHC(=S)R$_5$, NHC(=S)SR$_5$, NHC(=S)OR$_5$, and NHC(=O)SR$_5$.

Thus, in one embodiment, this invention provides or contemplates a compound of formula I, where NH—C(=X)—(Y)$_q$—R$_5$ is NHC(=O)R$_5$.

In another embodiment, this invention provides or contemplates a compound of formula I, where NH—C(=X)—(Y)$_q$—R$_5$ is NHC(=S)R$_5$.

In another embodiment, this invention provides or contemplates a compound of formula I, where NH—C(=X)—(Y)$_q$—R$_5$ is NHC(=S)SR$_5$.

In another embodiment, this invention provides or contemplates a compound of formula I, where NH—C(=X)—(Y)$_q$—R$_5$ is each NHC(=O)OR$_5$.

In another embodiment, this invention provides or contemplates a compound of formula I, where NH—C(=X)—(Y)$_q$—R$_5$ is NHC(=S)OR$_5$.

In another embodiment, this invention provides or contemplates a compound of formula I, where NH—C(=X)—(Y)$_q$—R$_5$ is NHC(=O)SR$_5$.

In a more specific embodiment, this invention provides or contemplates a compound of formula I, where R$_5$ is $C_1$-$C_6$ alkyl, (CHR$_6$)$_w$$C_3$-$C_6$ cycloalkyl, (CHR$_6$)$_w$CH$_2$$C_3$-$C_6$ cycloalkyl, or CH$_2$(CHR$_6$)$_w$$C_3$-$C_6$ cycloalkyl.

In a still more specific embodiment, this invention provides or contemplates a compound of formula I, where R$_5$ is $C_5$-$C_6$ alkyl, (CH$_2$)$_w$$C_5$-$C_6$ cycloalkyl, or (CHR$_6$)$_w$CH$_2$$C_5$-$C_6$ cycloalkyl.

In another more specific embodiment, this invention provides or contemplates a compound of formula I, where R$_5$ is $C_5$-$C_6$ alkyl, optionally substituted with one or two OH groups.

In another subgeneric embodiment, this invention provides or contemplates a compound of formula IA below.

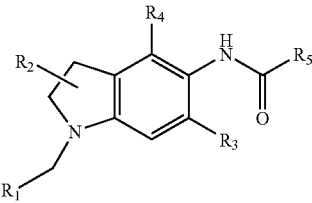

IA

In another subgeneric embodiment, this invention provides or contemplates a compound of formula IB below.

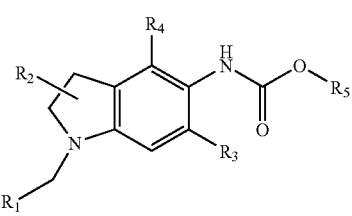

IB

In another subgeneric embodiment, this invention provides or contemplates a compound of formula IC below.

IC

[Structure IC shown]

In another subgeneric embodiment, this invention provides or contemplates a compound of formula ID below.

ID

[Structure ID shown]

In another subgeneric embodiment, this invention provides or contemplates a compound of formula IA, IB, IC, or ID, where $R_3$ and $R_4$ are, independently, methyl, chloro, or methoxy.

In another, more specific subgeneric embodiment, this invention provides or contemplates a compound of formula IA, IB, IC, or ID, where $R_3$ and $R_4$ are both methyl.

In another more specific subgeneric embodiment, this invention provides or contemplates a compound of formula IA, IB, IC, or ID, where $R_1$ is phenyl, substituted with halogen, cyano, $CF_3$, or methoxy, $R_2$ is H or methyl, and $R_5$ is $C_5$-$C_6$ alkyl or $CH_2$—$C_3$-$C_6$ cycloalkyl.

In another more specific subgeneric embodiment, this invention provides or contemplates a compound of formula IA, IB, IC, or ID, where $R_1$ is substituted phenyl or unsubstituted phenyl.

In another more specific subgeneric embodiment, this invention provides or contemplates a compound of formula IA, IB, IC, or ID, where $R_1$ is phenyl, substituted with halogen.

In a still more specific subgeneric embodiment, this invention provides or contemplates a compound of formula IA, IB, IC, or ID, where $R_1$ is fluorophenyl, or difluorophenyl.

In another more specific subgeneric embodiment, this invention provides or contemplates a compound of formula IA, IB, IC, or ID, where $R_1$ is phenyl, substituted with trifluoromethyl.

In another more specific subgeneric embodiment, this invention provides or contemplates a compound of formula IA, IB, IC, or ID, where $R_1$ is halophenyl, and $R_5$ is $C_5$-$C_6$ alkyl or $CH_2$—$C_5$-$C_6$ cycloalkyl.

In another more specific subgeneric embodiment, this invention provides or contemplates a compound of formula IA, IB, IC, or ID, where $R_1$ is halophenyl and $R_5$ is $CH_2$—$C_4$-alkyl or $CH_2$—$C_5$— alkyl.

In another more specific embodiment, this invention provides or contemplates a compound of formula IA, IB, IC, or ID, where $R_1$ is halo pyridyl.

In another more specific embodiment, this invention provides or contemplates a compound of formula IA or IC, where $R_1$ is dihalophenyl or dihalopyridyl; $R_2$ is H; and $R_3$ and $R_4$ are $C_1$, $CF_3$, or $CH_3$.

In another more specific embodiment, this invention provides or contemplates a compound of formula IB or ID, where $R_1$ is dihalophenyl or dihalopyridyl; $R_2$ is H; and $R_3$ and $R_4$ are $C_1$, $CF_3$, or $CH_3$.

In another more specific embodiment, this invention provides or contemplates a compound of formula IB or ID, where $R_1$ is halophenyl or halopyridyl; $R_2$ is H; and $R_3$ and $R_4$ are $C_1$, $CF_3$, or $CH_3$.

In another more specific embodiment, this invention provides or contemplates a compound of formula IA or IC, where $R_1$ is 3,5-dichlorophenyl or 3,5-difluorophenyl.

In another more specific embodiment, this invention provides or contemplates a compound of formula IB or ID, where $R_1$ is 3,5-dichlorophenyl or 3,5-difluorophenyl.

In another embodiment, this invention provides or contemplates a compound of formula I, in which $R_5$ is $C_1$-$C_6$ alkyl, where the $C_1$-$C_6$ alkyl group is substituted with one or two groups selected, independently, from OH, OMe, OEt, F, $CF_3$, Cl, or CN.

In another embodiment, this invention provides or contemplates a compound of formula I, in which X is S, q is zero, $R_1$ is substituted phenyl, $R_2$ is H, and $R_5$ is $C_1$-$C_6$ alkyl.

In another embodiment, this invention provides or contemplates a compound of formula I, in which X is S, q is zero, $R_1$ is substituted phenyl, $R_2$ is H, and $R_5$ is $C_1$-$C_6$ alkyl.

In yet another embodiment, this invention provides or contemplates a compound of formula I, in which X is S, q is 1, Y is O, $R_1$ is substituted phenyl, $R_2$ is H, and $R_5$ is $C_1$-$C_6$ alkyl.

In yet another embodiment, this invention provides or contemplates a compound of formula I, in which X is S, q is 1, Y is S, $R_1$ is substituted phenyl, $R_2$ is H, and $R_5$ is $C_1$-$C_6$ alkyl.

DETAILED DESCRIPTION OF THE INVENTION

In designing compounds with therapeutic properties superior to those of retigabine, shown below,

[Structure of retigabine shown]

retigabine and in optimizing the desirable therapeutic properties of this compound, the present inventors have discovered that compounds of formula I have surprising and exceptional activity toward potassium channels, as evidenced by potent activity, as measured in the rubidium (Rb+) efflux assay described below.

The inventors have further discovered that substitution at both the 2- and 6-positions of the central benzene ring confers a number of desirable properties, including both increased potency and increased stability in vivo. Thus, 2,6-di-substitution is a critical feature of some embodiments of this invention.

The inventors have further discovered that, in particular, alkyl substitution at both the 2- and 6-positions of the central benzene ring confers desirable properties, including both increased potency and increased stability in vivo. Thus, 2,6-dimethyl substitution is a critical feature of one embodiment of this invention.

Moreover, the inventors have also discovered that substitution with alkoxide groups at both the 2- and 6-positions of the central benzene ring also confers a number of desirable properties, including both increased potency and increased stability in vivo. Thus, such substitution is a critical feature of another embodiment of this invention.

Moreover, the inventors have also discovered that substitution at the 2- and 6-positions of the central benzene ring with substituents chosen from halogen, trifluoromethyl, and methoxy also confers a number of desirable properties, including both increased potency and increased stability in vivo. Thus, such substitution is a critical feature of yet another embodiment of this invention.

Among the embodiments of this invention, the most active compounds display a 40- to 400-fold improvement over retigabine, with the most promising compounds displaying $EC_{50}$s in the single-digit nanomolar range. Activities of several compounds of this invention are shown in Table 1 below. The activity of retigabine is shown for comparative purposes.

As used herein the term "potassium channel modulator" refers to a compound capable of causing an increase in potassium channel currents. It also refers to a compound capable of increasing the KCNQ2/3 channel open probability. For preliminary testing of compounds for potassium channel modulating ability, the inventors have employed the rubidium ion efflux test described below.

As contemplated by this invention, compounds of formula I are designed for oral or intravenous dosing of up to approximately 2000 mg per day. Thus, this invention contemplates solutions and suspensions of compounds of formula I formulated for intravenous administration. Similarly, solutions and suspensions comprising a syrup such as sorbitol or propylene glycol, among many other examples, in addition to compounds of formula I, suitable for oral pediatric administration, are also contemplated. Additionally, both chewable and non-chewable tablets comprising compounds of formula I, along with pharmaceutically acceptable tabletting agents and other pharmaceutically acceptable carriers and excipients, are also contemplated.

As used herein, the term "pharmaceutically acceptable carrier" comprises such excipients, binders, lubricants, tabletting agents and disintegrants as are typically used in the art of formulation of pharmaceuticals. Examples of such agents include—but are not limited to—microcrystalline cellulose, lactose, starch, and dicalcium phosphate, and Providone. However, in view of the incompatibility of primary amines with lactose, this invention does not contemplate compositions in which active ingredients with primary amine groups are combined with lactose. Additionally, disintegrants such as sodium starch glycolate, lubricants such as stearic acid and $SiO_2$, and solubility enhancers such as cyclodextrins, among many other examples for each group, are contemplated. Such materials and the methods of using them are well known in the pharmaceutical art. Additional examples are provided in Kibbe, *Handbook of Pharmaceutical Excipients*, London, Pharmaceutical Press, 2000.

The invention also contemplates pharmaceutical formulations for administration to animals, comprising a therapeutically effective amount of a compound of formula I and a veterinary acceptable carrier. Any animal that is susceptible to seizure disorders is included within the scope of this invention.

Synthetic Procedures

Section I. Preparation of compounds of formula XIV is outlined in Scheme 1.

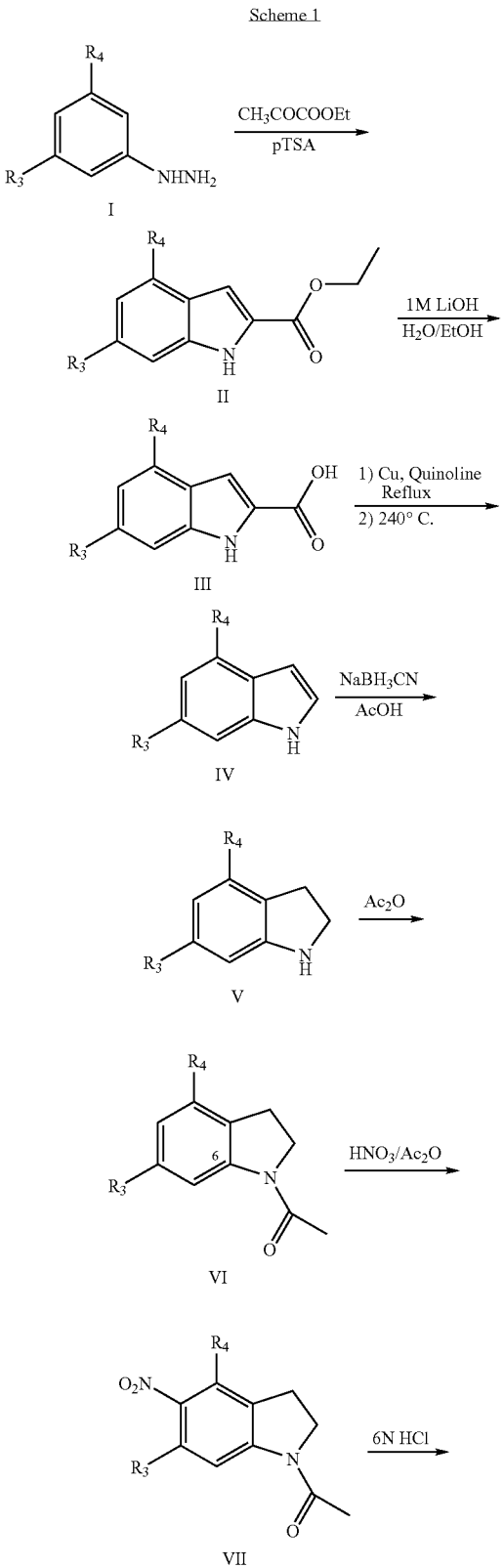

-continued
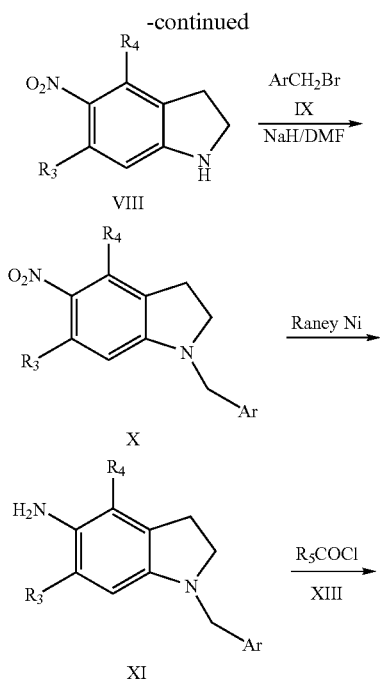
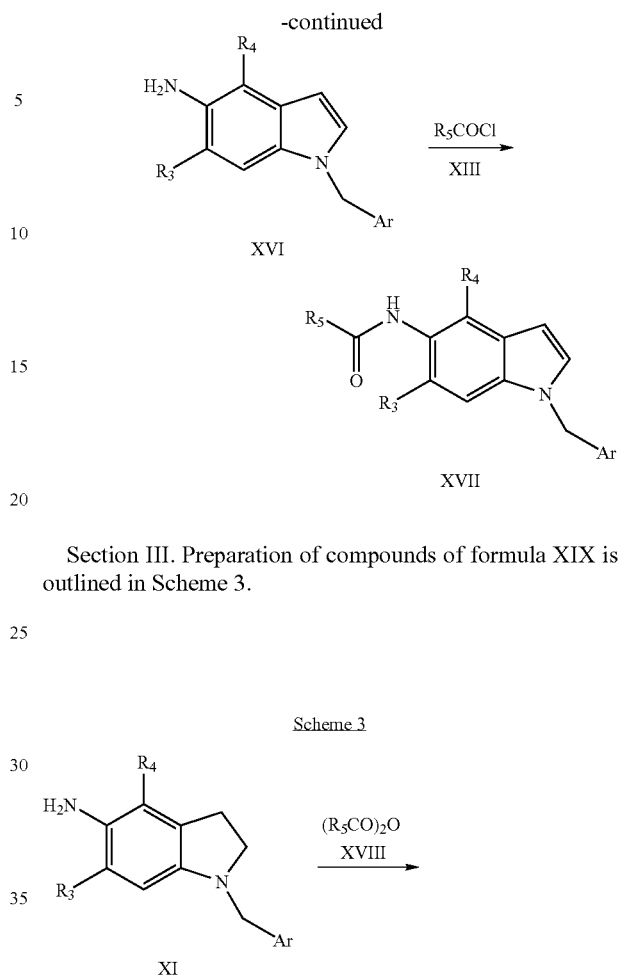
Section III. Preparation of compounds of formula XIX is outlined in Scheme 3.
Section II. Preparation of compounds of formula IX is outlined in Scheme 2.
Scheme 2
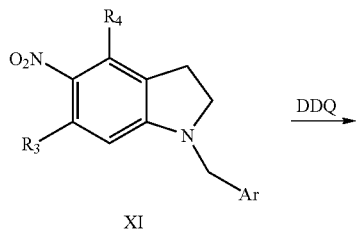
Section IV. Preparation of compounds of formula XX is outlined in Scheme 4.
Scheme 4
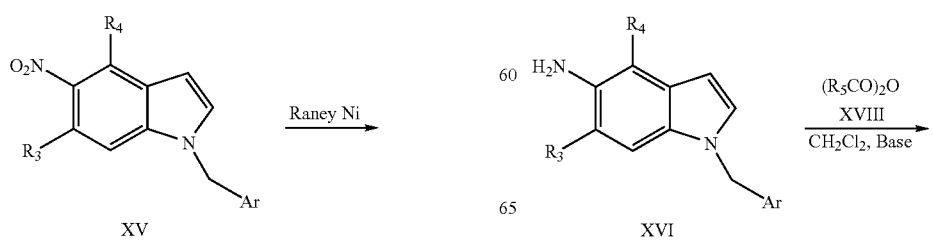

-continued

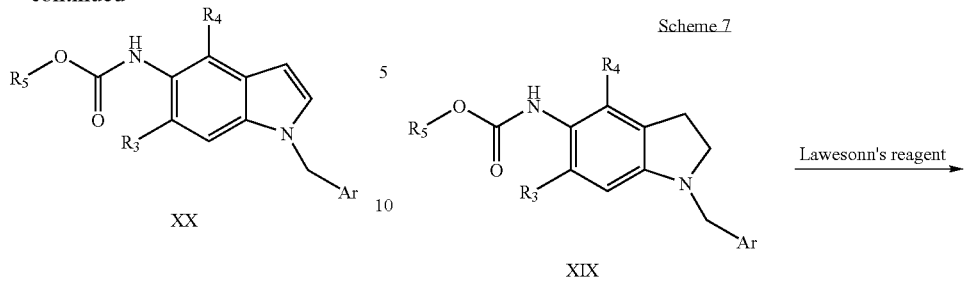

Section V. Preparation of compounds of formula XXI is outlined in Scheme 5.

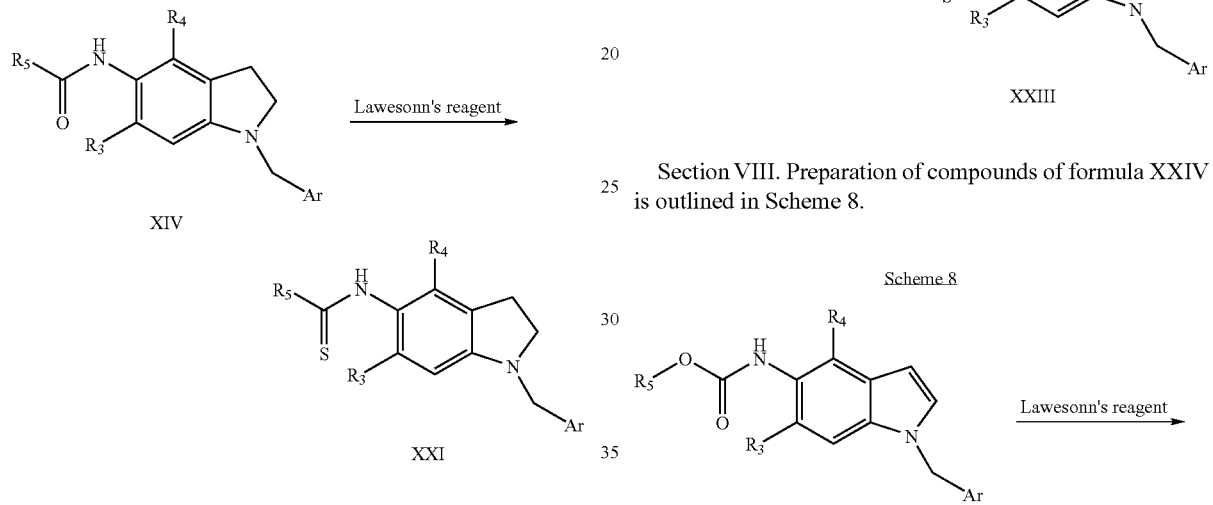

Section VI. Preparation of compounds of formula XXII is outlined in Scheme 6.

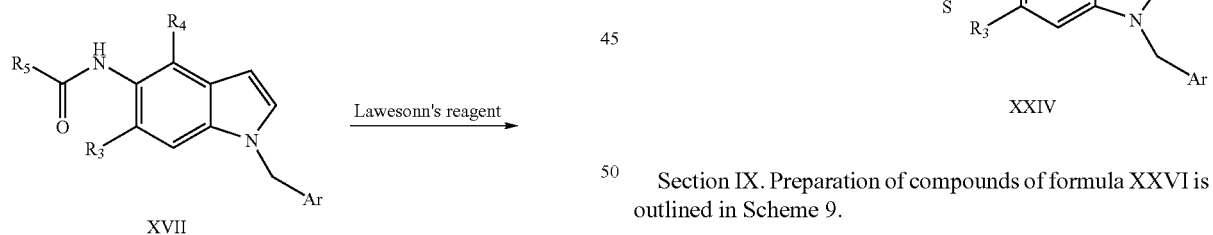

Section VII. Preparation of compounds of formula XXIII is outlined in Scheme 7.

Section VIII. Preparation of compounds of formula XXIV is outlined in Scheme 8.

Section IX. Preparation of compounds of formula XXVI is outlined in Scheme 9.

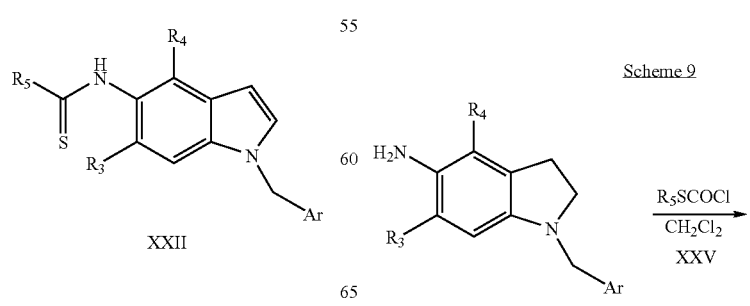

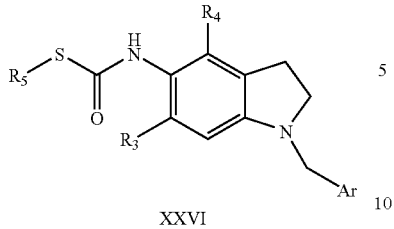

XXVI

Section X. Preparation of compounds of formula XXVII is outlined in Scheme 10.

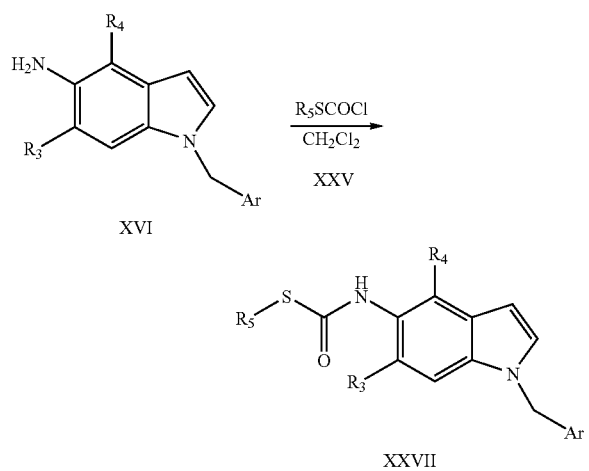

XXVII

4,6-Dimethyl-1H-indole-2-carboxylic acid ethyl ester (2)

In a flask fitted with a Dean-Stark trap, p-toluenesulfonic acid monohydrate (132 g, 0.69 mol) in 500 ml of benzene was heated at reflux for 2 hours. A solution of 3,5-dimethylphenylhydrazine hydrochloride (34.5 g, 0.2 mol), ethyl pyruvate (23.2 g, 0.2 mol), and p-toluenesulfonic acid monohydrate (0.85 g, 0.005 mol) in 500 ml of benzene, which had been refluxed for 2 hours with water removed through a Dean-Stark apparatus was then added. The resulting mixture was heated at reflux and stirred overnight. After cooling, the solution was treated with saturated sodium bicarbonate solution and diluted with methylene chloride. The organic portion was washed twice with saturated sodium bicarbonate solution, dried over anhydrous sodium sulfate, and concentrated under reduced pressure. The residue was purified by ISCO (hexane/EtOAc, 0-30%, 40 min) to give yellow solids, which was recrystallized from hexane/ethyl acetate (10%) to give colorless needles (35.6 g, 82%). $^1$H NMR (DMSO-d$_6$, 400 MHz): δ 11.68 (brs, 1H, exchangeable with D$_2$O, NH), 7.12 (s, 1H), 7.05 (s, 1H), 6.71 (s, 1H), 4.33 (q, J=6.8 Hz, 2H), 2.44 (s, 3H), 2.35 (s, 3H), 1.34 (t, J=6.8 Hz, 3H).

4,6-Dimethyl-1H-indole-2-carboxylic acid (3)

A mixture of 4,6-dimethyl-1H-indole-2-carboxylic acid ethyl ester (22 g, 0.1 mol) and lithium hydroxide (4.8 g, 0.2 mol) in 400 ml of ethanol was heated at reflux overnight. The solvent was removed under reduced pressure and the residue was dissolved in water and neutralized with 10% HCl to pH<3. The resulting precipitates were filtered and washed with water and dried in vacuo at 40° C. to give white solids (18 g, 95%). $^1$H NMR (DMSO-d$_6$, 400 MHz): δ 12.73 (brs, 1H, exchangeable with D$_2$O, NH), 11.55 (brs, 1H, exchangeable with D$_2$O, NH), 7.06 (s, 1H), 7.03 (s, 1H), 6.69 (s, 1H), 2.44 (s, 3H), 2.35 (s, 3H).

4,6-Dimethyl-1H-indole (4)

Method A: A mixture of 4,6-dimethyl-1H-indole-2-carboxylic acid (3.61 g, 19.09 mmol, 1 equiv), copper powder (850 mg, 13.36 mmol, 0.7 equiv), and freshly distilled quinoline (50 mL) were brought at reflux for 2 h. The mixture was then cooled and filtered on Celite. The filtrate was poured on ice, and the solution was brought to pH 4 with concentrated HCl and extracted with ethyl acetate (3×100 ml). The combined extracts were washed with 2 N HCl (3×100 mL), saturated NaHCO$_3$, and brine. The organic solution was dried over MgSO$_4$ and concentrated. The residue was flash chromatographed on silica gel using hexane-AcOEt (85-15) to give a white solid (2.6 g, 94%). $^1$H NMR (DMSO-d$_6$, 400 MHz): δ 10.8 (brs, 1H, exchangeable with D$_2$O, NH), 7.19 (t, J=2 Hz, 1H), 6.99 (s, 1H), 6.62 (s, 1H), 6.36 (t, J=2 Hz, 1H), 2.41 (s, 3H), 2.34 (s, 3H).

Method 2: This indole also was prepared heating 26 g (0.14 mol) of 4,6-dimethyl-1H-indole-2-carboxylic acid to 230° C. for 3 hours. After cooling, the reactant was distilled under reduced pressure (2.9-4.4 mmHg) at 130-135° C. to give a pure product as colorless oil (15.6 g, 77%).

4,6-Dimethylindoline (5) and 1-Acetyl-4,6-dimethylindoline (6) are prepared by the following procedure.

4,6-Dimethylindole (1.08 g) was dissolved in acetic acid (20 ml), and sodium cyanoborohydride (2.3 g) was added portionwise at 15° C. The mixture was stirred at said temperature for one hour and poured into ice water. Saturated aqueous sodium bicarbonate was added to neutralize the mixture and the mixture was extracted with ethyl acetate. The extract was washed with saturated brine and dried over sodium sulfate. The solvent was evaporated under reduced pressure. The residue was dissolved in benzene, and acetic anhydride (840 mg) was added, which was followed by stirring at room temperature for one hour. The reaction mixture was washed with saturated aqueous sodium bicarbonate and saturated brine, and dried over sodium sulfate. The solvent was evaporated under reduced pressure. The residue was chromatographed (ISCO, hexane/EtOAc, 0-40%, 40 min) to give 1.3 g of 1-acetyl-4,6-dimethylindoline.

$^1$H-NMR (CDCl$_3$) δ: 2.18 (6H, s), 2.30 (3H, s), 3.00 (2H, t, J=8.3 Hz), 4.03 (2H, t, J=8.3 Hz), 6.66 (1H, s), 7.89 (1H, s).

1-Acetyl-4,6-dimethyl-5-nitroindoline (7) was prepared as follows.

1-Acetyl-4,6-dimethylindoline (2.6 g) was dissolved in acetic anhydride (35 ml), and nitric acid (d=1.5, 0.92 ml) dissolved in acetic anhydride (15 ml) was added dropwise at 0° C. The mixture was stirred at room temperature for one hour and poured into ice water. Saturated aqueous sodium bicarbonate was added to neutralize the mixture, and the mixture was extracted with chloroform. The extract was washed with saturated brine and dried over sodium sulfate. The solvent was evaporated under reduced pressure. The residue was chromatographed (ISCO, hexane/EtOAc, 0-40%, 40 min) to give 2.4 g of white solids. $^1$H NMR (DMSO-d$_6$, 400 MHz): δ 6.95 (s, 1H), 4.19 (t, J=8.0 Hz, 2H), 3.04 (t, J=8.0 Hz, 2H), 2.26 (s, 3H), 2.23 (s, 3H), 2.18 (s, 3H).

4,6-Dimethyl-5-nitroindoline (8) was prepared by the following procedure.

1-Acetyl-4,6-dimethyl-5-nitroindoline (2.4 g) was dissolved in methanol (25 ml). Hydrochloric acid 6N (20 ml) was added, followed by reflux for 15 hours. After the completion of the reaction, the solvent was evaporated under reduced pressure. The residue was dissolved in chloroform, and the mixture was washed with saturated aqueous sodium bicarbonate and saturated brine, and dried over sodium sulfate. The solvent was evaporated under reduced pressure. The residue was chromatographed (ISCO, hexane/EtOAc, 0-40%, 40 min) to give 1.8 g of 4,6-dimethyl-5-nitroindoline as yellow solids. $^1$H NMR (DMSO-$d_6$, 400 MHz): δ 6.36 (brs, 1H, exchangeable with $D_2O$, NH), 6.20 (s, 1H), 3.54 (t, J=8.0 Hz, 2H), 2.91 (t, J=8.0 Hz, 2H), 2.17 (s, 3H), 2.10 (s, 3H).

4,6-Dimethyl-5-nitro-1-(4-trifluoromethyl-benzyl)-indoline (9): R=CF₃

4,6-dimethyl-5-nitroindoline (0.33 g, 1.7 mmol) was dissolved in dimethylformamide (10 ml), and sodium hydride (ca. 60% in oil suspension, 136 mg) was added at 0° C. The mixture was stirred at 0° C. for 0.5 hour and 4-trifluoromethylbenzyl bromide (0.48 g, 2 mmol)) was added to the reaction mixture, which was followed by stirring at room temperature overnight. Water was added to the reaction mixture, and the mixture was extracted with ethyl acetate. The extract was washed with saturated brine and dried over sodium sulfate. The solvent was evaporated under reduced pressure. The residue was chromatographed (ISCO, hexane/EtOAc, 0-40%, 40 min) to give yellow solids (0.55 g, 92%). $^1$H NMR (DMSO-$d_6$, 400 MHz): δ 7.73 (d, J=8.0 Hz, 2H), 7.52 (d, J=8.0 Hz, 2H), 6.41 (s, 1H), 4.52 (s, 2H), 3.50 (t, J=8.0 Hz, 2H), 2.95 (t, J=8.0 Hz, 2H), 2.20 (s, 3H), 2.11 (s, 3H).

The following compounds were prepared by the above procedure:
4,6-Dimethyl-5-nitro-1-(4-fluorobenzyl)-indoline
4,6-Dimethyl-5-nitro-1-(3-chlorobenzyl)-indoline
4,6-Dimethyl-5-nitro-1-(4-bromobenzyl)-indoline
4,6-Dimethyl-5-nitro-1-(3,4-difluorobenzyl)-indoline
4,6-Dimethyl-5-nitro-1-(naphthalen-2-ylmethyl)-indoline
4,6-Dimethyl-5-nitro-1-(pyridin-4-ylmethyl)-indoline
4,6-Dimethyl-5-nitro-1-(pyridin-3-ylmethyl)-indoline

4,6-Dimethyl-5-nitro-1-(4-(trifluoromethyl)benzyl)-1H-indole (12): R=CF₃

A solution of 4,6-dimethyl-5-nitro-1-(4-trifluoromethyl-benzyl)-indoline (350 mg, 1 mmol) and DDQ (454 mg, 2 mmol) in 30 ml of anhydrous dioxane was stirred a 50° C. for 2 days. After cooling, the solvent was removed under reduced pressure and the residue was purified by silica gel column chromatography (ISCO, hexane/EtOAc, 0-40%, 40 min) to give yellow crystals (300 mg, 86%).

The following compounds were prepared by the above procedure.
4,6-Dimethyl-5-nitro-1-(4-fluorobenzyl)-1H-indole
4,6-Dimethyl-5-nitro-1-(4-chlorobenzyl)-1H-indole
4,6-Dimethyl-5-nitro-1-(4-bromobenzyl)-1H-indole
4,6-Dimethyl-5-nitro-1-(3,4-difluorobenzyl)-1H-indole
4,6-Dimethyl-5-nitro-1-(3,5-difluorobenzyl)-1H-indole

1-(4-Trifluoromethyl-benzyl)-4,6-dimethyl-5-aminoindoline (10): R=CF₃

1-(4-Trifluoromethyl-benzyl)-4,6-dimethyl-5-nitroindoline (1.0 g) was dissolved in methanol (40 ml) and catalytic amount of Raney Ni was added to allow hydrogenation at room temperature under regular pressure. After the completion of the reaction, catalyst was filtered off, and the filtrate was evaporated under reduced pressure to give the white solid product, which is pure enough for next step without further purification.

The following compounds were prepared by the above procedure:
1-(4-Fluorobenzyl)-4,6-dimethyl-5-amino indo line
1-(3-Chlorobenzyl)-4,6-dimethyl-5-amino indo line
1-(4-Bromobenzyl)-4,6-dimethyl-5-amino indo line
1-(3,4-Difluorobenzyl)-4,6-dimethyl-5-aminoindoline
1-(Naphthalen-2-ylmethyl)-4,6-dimethyl-5-amino indo line
1-(Pyridin-4-ylmethyl)-4,6-dimethyl-5-amino indo line
1-(Pyridin-3-ylmethyl)-4,6-dimethyl-5-amino indo line
4,6-Dimethyl-5-amino-1-(4-(trifluoromethyl)benzyl)-1H-indole
4,6-Dimethyl-5-amino-1-(4-fluorobenzyl)-1H-indole
4,6-Dimethyl-5-amino-1-(4-chlorobenzyl)-1H-indole
4,6-Dimethyl-5-amino-1-(4-bromobenzyl)-1H-indole
4,6-Dimethyl-5-amino-1-(3,4-difluorobenzyl)-1H-indole
4,6-Dimethyl-5-amino-1-(3,5-difluorobenzyl)-1H-indole

N-[1-(4-Trifluoromethyl-benzyl)-4,6-dimethylindoline-5-yl]-3,3-dimethyl-butyramide (11): R=CF₃

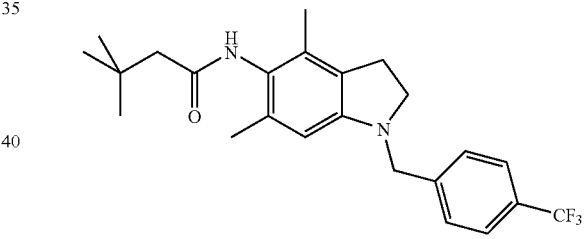

To a solution of 5-amino-4,6-dimethyl-1-(4-trifluoromethylbenzyl)indoline (0.26 g, 0.82 mmol) and triethylamine (125 mg, 1.24 mmol) in anhydrous methylene chloride (20 ml) was added dropwise tert-butyl acetyl chloride (135 mg, 1 mmol) at 0° C. The reaction mixture was stirred at room temperature for 18 hours. Water was added to the reaction mixture, and the mixture was washed with saturated brine and dried over sodium sulfate. The solvent was evaporated under reduced pressure. The residue was purified by silica gel column chromatography (ISCO, hexane/EtOAc, 0-40%, 40 min) and recrystallized from hexane/EtOAc (5:1) to give 290 mg (85%) of the white solids. $^1$H NMR (DMSO-$d_6$, 400 MHz): δ 8.80 (brs, 1H, exchangeable with $D_2O$, NH), 7.72 (d, J=8.0 Hz, 2H), 7.56 (d, J=8.0 Hz, 2H), 6.29 (s, 1H), 4.34 (s, 2H), 3.28 (t, J=8.0 Hz, 2H), 2.82 (t, J=8.0 Hz, 2H), 2.17 (s, 2H), 2.03 (s, 3H), 1.96 (s, 3H), 1.07 (s, 9H). MS: 419 (M+1).

The following compounds were prepared by the above procedure.

N-[1-(4-Fluorobenzyl)-4,6-dimethylindoline-5-yl]-3,3-dimethyl-butyramide

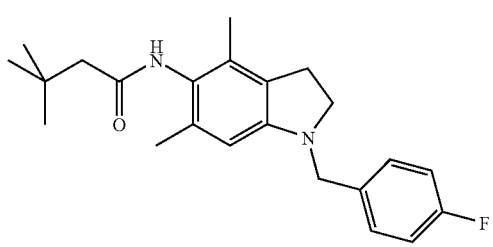

$^1$H NMR (DMSO-d$_6$, 400 MHz): δ 8.78 (brs, 1H, exchangeable with D$_2$O, NH), 7.37 (dd, J=8.8 and 5.7 Hz, 2H), 7.16 (t, J=8.8 Hz, 2H), 6.32 (s, 1H), 4.22 (s, 2H), 3.22 (t, J=8.0 Hz, 2H), 2.79 (t, J=8.0 Hz, 2H), 2.17 (s, 2H), 2.03 (s, 3H), 1.95 (s, 3H), 1.05 (s, 9H). MS: 369 (M+1).

N-[1-(3-Chlorobenzyl)-4,6-dimethylindoline-5-yl]-3,3-dimethyl-butyramide

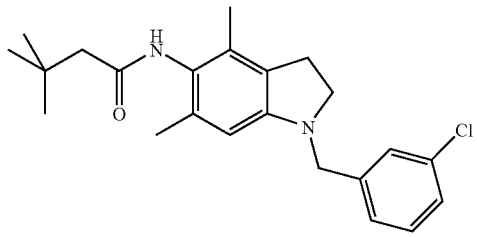

$^1$H NMR (DMSO-d$_6$, 400 MHz): δ 8.79 (brs, 1H, exchangeable with D$_2$O, NH), 7.34 (m, 4H), 6.29 (s, 1H), 4.25 (s, 2H), 3.26 (t, J=8.0 Hz, 2H), 2.81 (t, J=8.0 Hz, 2H), 2.17 (s, 2H), 2.03 (s, 3H), 1.96 (s, 3H), 1.05 (s, 9H). MS: 385 (M+1).

N-[1-(4-Bromobenzyl)-4,6-dimethylindoline-5-yl]-3,3-dimethyl-butyramide

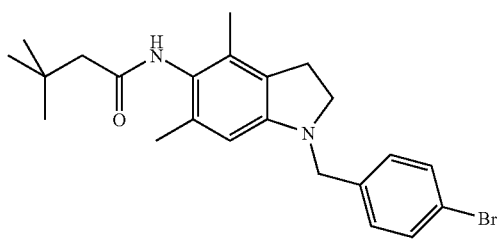

$^1$H NMR (DMSO-d$_6$, 400 MHz): δ 8.78 (brs, 1H, exchangeable with D$_2$O, NH), 7.54 (d, J=8.0 Hz, 2H), 7.30 (d, J=8.0 Hz, 2H), 6.29 (s, 1H), 4.21 (s, 2H), 3.24 (t, J=8.0 Hz, 2H), 2.80 (t, J=8.0 Hz, 2H), 2.17 (s, 2H), 2.02 (s, 3H), 1.95 (s, 3H), 1.05 (s, 9H). MS: 429 (M+1).

N-[1-(3,4-Difluorobenzyl)-4,6-dimethylindoline-5-yl]-3,3-dimethyl-butyramide

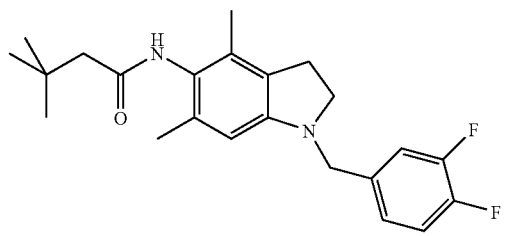

$^1$H NMR (DMSO-d$_6$, 400 MHz): δ 8.79 (brs, 1H, exchangeable with D$_2$O, NH), 7.41 (m, 2H), 7.19 (m, 1H), 6.30 (s, 1H), 4.22 (s, 2H), 3.25 (t, J=8.0 Hz, 2H), 2.80 (t, J=8.0 Hz, 2H), 2.17 (s, 2H), 2.03 (s, 3H), 1.96 (s, 3H), 1.05 (s, 9H). MS: 387 (M+1).

N-(4,6-Dimethyl-1-(naphthalen-2-ylmethyl)indolin-5-yl)-3,3-dimethylbutanamide

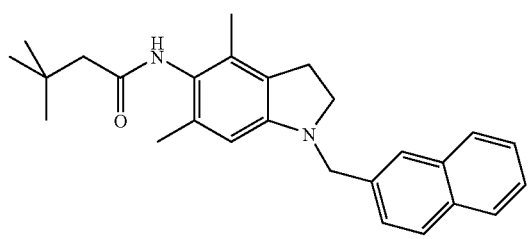

$^1$H NMR (DMSO-d$_6$, 400 MHz): δ 8.79 (brs, 1H, exchangeable with D$_2$O, NH), 7.89 (m, 4H), 7.50 (m, 3H), 6.35 (s, 1H), 4.39 (s, 2H), 3.29 (t, J=8.0 Hz, 2H), 2.84 (t, J=8.0 Hz, 2H), 2.17 (s, 2H), 2.03 (s, 3H), 1.97 (s, 3H), 1.05 (s, 9H). MS: 401 (M+1).

N-(4,6-Dimethyl-1-(pyridin-4-ylmethyl)indolin-5-yl)-3,3-dimethylbutanamide

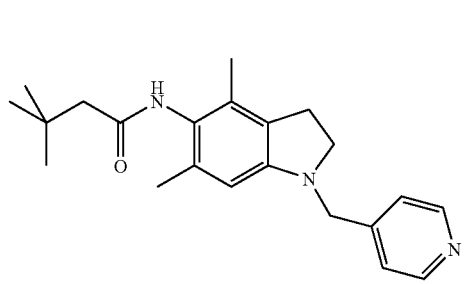

$^1$H NMR (DMSO-d$_6$, 400 MHz): δ 8.80 (brs, 1H, exchangeable with D$_2$O, NH), 8.52 (d, J=8.0 Hz, 2H), 7.34 (d, J=8.0 Hz, 2H), 6.25 (s, 1H), 4.28 (s, 2H), 3.30 (t, J=8.0 Hz, 2H), 2.84 (t, J=8.0 Hz, 2H), 2.17 (s, 2H), 2.03 (s, 3H), 1.97 (s, 3H), 1.05 (s, 9H). MS: 352 (M+1).

N-(4,6-Dimethyl-1-(pyridin-3-ylmethyl)indolin-5-yl)-3,3-dimethylbutanamide

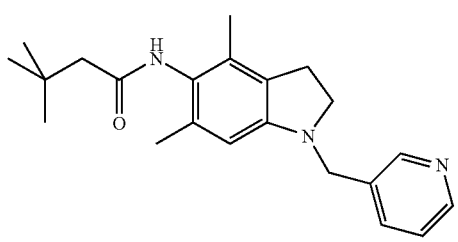

$^1$H NMR (DMSO-d$_6$, 400 MHz): δ 8.79 (brs, 1H, exchangeable with D$_2$O, NH), 8.57 (d, J=2.0 Hz, 1H), 8.49 (dd, J=2.0 and 4.4 Hz, 1H), 7.74 (d, J=8.0 Hz, 1H), 7.38 (dd, J=8.0 and 4.4 Hz, 1H), 6.36 (s, 1H), 4.27 (s, 2H), 3.24 (t, J=8.0 Hz, 2H), 2.79 (t, J=8.0 Hz, 2H), 2.17 (s, 2H), 2.04 (s, 3H), 1.95 (s, 3H), 1.05 (s, 9H). MS: 352 (M+1).

N-(4,6-Dimethyl-1-(4-(trifluoromethyl)benzyl)-1H-indol-5-yl)-3,3-dimethylbutanamide

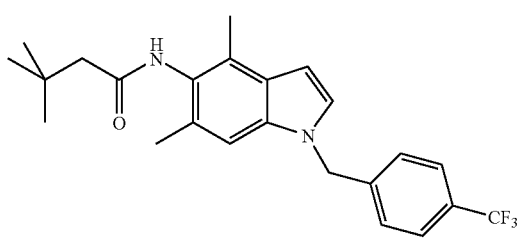

$^1$H NMR (DMSO-d$_6$, 400 MHz): δ 9.00 (brs, 1H, exchangeable with D$_2$O, NH), 7.67 (d, J=8.0 Hz, 2H), 7.41 (d, J=3.2 Hz, 1H), 7.29 (d, J=8.0 Hz, 2H), 7.09 (s, 1H), 6.50 (d, J=3.2 Hz, 1H), 5.50 (s, 2H), 2.29 (s, 2H), 2.22 (s, 3H), 2.19 (s, 3H), 1.07 (s, 9H). MS: 417 (M+1).

N-(4,6-Dimethyl-1-(4-(fluorobenzyl)-1H-indol-5-yl)-3,3-dimethylbutanamide

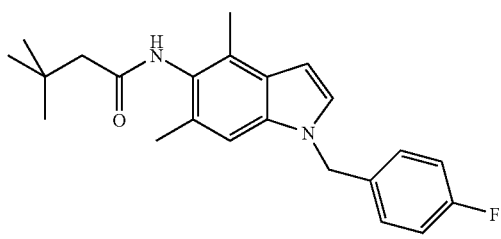

$^1$H NMR (DMSO-d$_6$, 400 MHz): δ 8.99 (brs, 1H, exchangeable with D$_2$O, NH), 7.39 (d, J=3.2 Hz, 1H), 7.21 (dd, J=8.8 and 5.7 Hz, 2H), 7.15 (t, J=8.8 Hz, 2H), 7.12 (s, 1H), 6.46 (d, J=3.2 Hz, 1H), 5.36 (s, 2H), 2.28 (s, 2H), 2.22 (s, 3H), 2.20 (s, 3H), 1.07 (s, 9H). MS: 367 (M+1).

N-(4,6-Dimethyl-1-(3,4-difluorobenzyl)-1H-indol-5-yl)-3,3-dimethylbutanamide

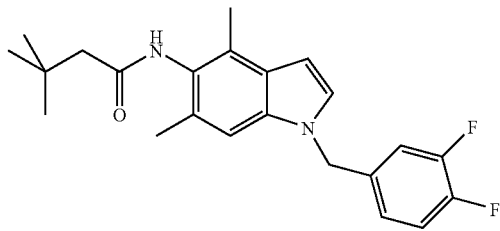

$^1$H NMR (DMSO-d$_6$, 400 MHz): δ 9.00 (brs, 1H, exchangeable with D$_2$O, NH), 7.41 (d, J=3.2 Hz, 1H), 7.35 (m, 1H), 7.23 (m, 1H), 7.14 (s, 1H), 6.95 (m, 1H), 6.48 (d, J=3.2 Hz, 1H), 5.36 (s, 2H), 2.28 (s, 2H), 2.22 (s, 3H), 2.20 (s, 3H), 1.07 (s, 9H). MS: 385 (M+1).

N-(4,6-Dimethyl-1-(3,5-difluorobenzyl)-1H-indol-5-yl)-3,3-dimethylbutanamide

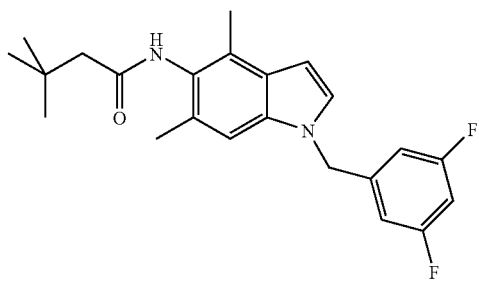

$^1$H NMR (DMSO-d$_6$, 400 MHz): δ 9.01 (brs, 1H, exchangeable with D$_2$O, NH), 7.43 (d, J=3.2 Hz, 1H), 7.13 (s, 1H), 7.10 (m, 1H), 6.81 (m, 2H), 6.49 (d, J=3.2 Hz, 1H), 5.40 (s, 2H), 2.29 (s, 2H), 2.22 (s, 3H), 2.21 (s, 3H), 1.08 (s, 9H). MS: 385 (M+1).

N-(4,6-Dimethyl-1-(3-chlorobenzyl)-1H-indol-5-yl)-3,3-dimethylbutanamide

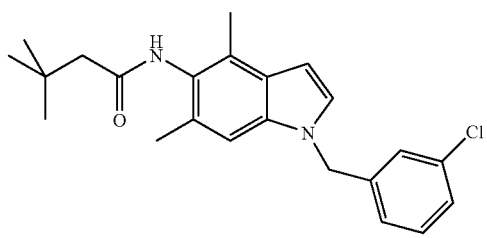

$^1$H NMR (DMSO-d$_6$, 400 MHz): δ 9.00 (brs, 1H, exchangeable with D$_2$O, NH), 7.41 (d, J=3.2 Hz, 1H), 7.31 (m, 2H), 7.19 (s, 1H), 7.12 (s, 1H), 7.03 (m, 1H), 6.95 (m, 1H), 6.49 (d, J=3.2 Hz, 1H), 5.39 (s, 2H), 2.29 (s, 2H), 2.22 (s, 3H), 2.20 (s, 3H), 1.08 (s, 9H). MS: 383 (M+1).

N-(4,6-Dimethyl-1-(4-bromobenzyl)-1H-indol-5-yl)-3,3-dimethylbutanamide

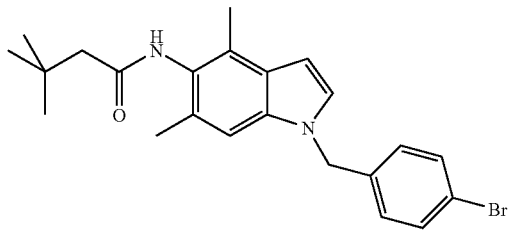

$^1$H NMR (DMSO-$d_6$, 400 MHz): δ 8.99 (brs, 1H, exchangeable with $D_2O$, NH), 7.49 (d, J=8.4 Hz, 2H), 7.38 (d, J=3.2 Hz, 1H), 7.08 (s, 1H), 7.07 (d, J=8.4 Hz, 1H), 6.47 (d, J=3.2 Hz, 1H), 5.36 (s, 2H), 2.28 (s, 2H), 2.19 (s, 3H), 2.17 (s, 3H), 1.07 (s, 9H). MS: 427 (M+1).

Biological Results

Compounds of this invention formula were evaluated as potassium channel modulators by measuring rhubidium ion release in the following assay.

Methods: PC-12 cells were grown at 37° C. and 5% $CO_2$ in DMEM/F12 Medium supplemented with 10% horse serum, 5% fetal bovine serum, 2 mM glutamine, 100 U/ml penicillin, 100 U/ml streptomycin. They were plated in poly-D-lysine-coated 96-well cell culture microplates at a density of 40,000 cells/well and differentiated with 100 ng/ml NGF-7s for 2-5 days. For the assay, the medium was aspirated and the cells were washed once with 0.2 ml in wash buffer (25 mM HEPES, pH 7.4, 150 mM NaCl, 1 mM $MgCl_2$, 0.8 mM $NaH_2PO_4$, 2 mM $CaCl_2$). The cells were then loaded with 0.2 ml $Rb^+$ loading buffer (wash buffer plus 5.4 mM $RbCl_2$, 5 mM glucose) and incubated at 37° C. for 2 h. Attached cells were quickly washed three times with buffer (same as $Rb^+$ loading buffer, but containing 5.4 mM KCl instead of RbCl) to remove extracellular $Rb^+$. Immediately following the wash, 0.2 ml of depolarization buffer (wash buffer plus 15 mM KCl) with or without compounds was added to the cells to activate efflux of potassium ion channels. After incubation for 10 min at room temperature, the supernatant was carefully removed and collected. Cells were lysed by the addition of 0.2 ml of lysis buffer (depolarization buffer plus 0.1% Triton X-100) and the cell lysates were also collected. If collected samples were not immediately analyzed for $Rb^+$ contents by atomic absorption spectroscopy (see below), they were stored at 4° C. without any negative effects on subsequent $Rb^+$ analysis.

The concentration of $Rb^+$ in the supernatants ($Rb^+_{Sup}$) and cell lysates ($Rb^+_{Lys}$) was quantified using an ICR8000 flame atomic absorption spectrometer (Aurora Biomed Inc., Vancouver, B.C.) under conditions defined by the manufacturer. One 0.05 ml samples were processed automatically from microtiter plates by dilution with an equal volume of $Rb^+$ sample analysis buffer and injection into an air-acetylene flame. The amount of $Rb^+$ in the sample was measured by absorption at 780 nm using a hollow cathode lamp as light source and a PMT detector. A calibration curve covering the range 0-5 mg/L $Rb^+$ in sample analysis buffer was generated with each set of plates. The percent $Rb^+$ efflux (F) was defined by $$F=[Rb^+_{Sup}/(Rb^+_{Sup}+Rb^+_{Lys})]\times 100\%.$$

The effect (E) of a compound was defined by:

$$E=[(F_c-F_b)/(F_s-F_b)]\times 100\%$$

where the $F_c$ is the efflux in the presence of compound in depolarization buffer, $F_b$ is the efflux in basal buffer, and FS is the efflux in depolarization buffer, and $F_c$ is the efflux in the presence of compound in depolarization buffer. The effect (E) and compound concentration relationship was plotted to calculate an $EC_{50}$ value, a compound's concentration for 50% of maximal $Rb^+$ efflux. The results are shown below. Legend: A: EC50=1 nM-50 nM; B: EC50=50 nM-100 nM; C: EC50=100 nM-200 nM; D: EC50=200 nM-500 nM.

TABLE 1

ACTIVITIES OF EXEMPLARY COMPOUNDS

| COMPOUND | ACTIVITY |
|---|---|
| (structure: 4,6-dimethyl-indoline with 3,3-dimethylbutanamide at 5-position, N-(4-CF3-benzyl)) | A |
| (structure: 4,6-dimethyl-indoline with 3,3-dimethylbutanamide at 5-position, N-(4-F-benzyl)) | A |
| (structure: 4,6-dimethyl-indoline with 3,3-dimethylbutanamide at 5-position, N-(3-Cl-benzyl)) | A |
| (structure: 4,6-dimethyl-indoline with 3,3-dimethylbutanamide at 5-position, N-(4-Br-benzyl)) | A |
| (structure: 4,6-dimethyl-indoline with 3,3-dimethylbutanamide at 5-position, N-(3,4-diF-benzyl)) | A |

TABLE 1-continued
ACTIVITIES OF EXEMPLARY COMPOUNDS

| COMPOUND | ACTIVITY |
|---|---|
| (indoline with 2-naphthylmethyl N-substituent, 4,6-dimethyl, 5-(3,3-dimethylbutanamido)) | A |
| (indoline with pyridin-4-ylmethyl N-substituent, 4,6-dimethyl, 5-(3,3-dimethylbutanamido)) | D |
| (indoline with 3,5-difluorobenzyl N-substituent, 4,6-dimethyl, 5-(3,3-dimethylbutanamido)) | A |
| (indole with 4-trifluoromethylbenzyl N-substituent, 4,6-dimethyl, 5-(3,3-dimethylbutanamido)) | A |
| (indole with 4-fluorobenzyl N-substituent, 4,6-dimethyl, 5-(3,3-dimethylbutanamido)) | A |
| (indole with 3,4-difluorobenzyl N-substituent, 4,6-dimethyl, 5-(3,3-dimethylbutanamido)) | A |
| (indole with 3,5-difluorobenzyl N-substituent, 4,6-dimethyl, 5-(3,3-dimethylbutanamido)) | A |
| (indole with 3-chlorobenzyl N-substituent, 4,6-dimethyl, 5-(3,3-dimethylbutanamido)) | A |
| (indole with 4-chlorobenzyl N-substituent, 4,6-dimethyl, 5-(3,3-dimethylbutanamido)) | A |
| (retigabine) | C |

What is claimed is:

1. A compound which is one of the following:
   N-[1-(4-Trifluoromethylbenzyl)-4,6-dimethylindoline-5-yl]-3,3-dimethyl-butyramide
   N-[1-(4-Fluorobenzyl)-4,6-dimethylindoline-5-yl]-3,3-dimethyl-butyramide
   N-[1-(3-Chlorobenzyl)-4,6-dimethylindoline-5-yl]-3,3-dimethyl-butyramide
   N-[1-(4-Bromobenzyl)-4,6-dimethylindoline-5-yl]-3,3-dimethyl-butyramide
   N-[1-(3,4-Difluorobenzyl)-4,6-dimethylindoline-5-yl]-3,3-dimethyl-butyramide
   N-(4,6-Dimethyl-1-(naphthalen-2-ylmethyl)indolin-5-yl)-3,3-dimethylbutanamide
   N-(4,6-Dimethyl-1-(pyridin-4-ylmethyl)indolin-5-yl)-3,3-dimethylbutanamide
   N-(4,6-Dimethyl-1-(pyridin-3-ylmethyl)indolin-5-yl)-3,3-dimethylbutanamide
   N-(4,6-Dimethyl-1-(4-(trifluoromethyl)benzyl)-1H-indol-5-yl)-3,3-dimethyl butanamide N-(4,6-Dimethyl-1-(4-(fluorobenzyl)-1H-indol-5-yl)-3,3-dimethylbutanamide N-(4,6-Dimethyl-1-(3,4-difluorobenzyl)-1H-indol-5-yl)-3,3-dimethylbutanamide N-(4,6-Dimethyl-1-(3,5-difluorobenzyl)-1H-indol-5-yl)-3,3-dimethylbutanamide N-(4,6-Dimethyl-1-(3-chlorobenzyl)-1H-indol-5-yl)-3,3-dimethylbutanamide and N-(4,6-Dimethyl-1-(4-bromobenzyl)-1H-indol-5-yl)-3,3-dimethylbutanamide.

2. The compound of claim 1 that is N-[1-(4-Trifluoromethylbenzyl)-4,6-dimethylindoline-5-yl]-3,3-dimethyl-butyramide.

3. The compound of claim 1 that is N-[1-(4-Fluorobenzyl)-4,6-dimethylindoline-5-yl]-3,3-dimethyl-butyramide.

4. The compound of claim 1 that is N-[1-(3-Chlorobenzyl)-4,6-dimethylindoline-5-yl]-3,3-dimethyl-butyramide.

5. The compound of claim 1 that is N-[1-(4-Bromobenzyl)-4,6-dimethylindoline-5-yl]-3,3-dimethyl-butyramide.

6. The compound of claim 1 that is N-[1-(3,4-Difluorobenzyl)-4,6-dimethylindoline-5-yl]-3,3-dimethyl-butyramide.

7. The compound of claim 1 that is N-(4,6-Dimethyl-1-(naphthalen-2-ylmethyl)indolin-5-yl)-3,3-dimethylbutanamide.

8. The compound of claim 1 that is N-(4,6-Dimethyl-1-(pyridin-4-ylmethyl)indolin-5-yl)-3,3-dimethylbutanamide.

9. The compound of claim 1 that is N-(4,6-Dimethyl-1-(pyridin-3-ylmethyl)indolin-5-yl)-3,3-dimethylbutanamide.

10. The compound of claim 1 that is N-(4,6-Dimethyl-1-(4-(trifluoromethyl)benzyl)-1H-indol-5-yl)-3,3-dimethyl butanamide.

11. The compound of claim 1 that is N-(4,6-Dimethyl-1-(4-(fluorobenzyl)-1H-indol-5-yl)-3,3-dimethylbutanamide.

12. The compound of claim 1 that is N-(4,6-Dimethyl-1-(3,4-difluorobenzyl)-1H-indol-5-yl)-3,3-dimethylbutanamide.

13. The compound of claim 1 that is N-(4,6-Dimethyl-1-(3,5-difluorobenzyl)-1H-indol-5-yl)-3,3-dimethylbutanamide.

14. The compound of claim 1 that is N-(4,6-Dimethyl-1-(3-chlorobenzyl)-1H-indol-5-yl)-3,3-dimethylbutanamide.

15. The compound of claim 1 that is N-(4,6-Dimethyl-1-(4-bromobenzyl)-1H-indol-5-yl)-3,3-dimethylbutanamide.

* * * * *